United States Patent
Kitahara et al.

(10) Patent No.: US 9,465,033 B2
(45) Date of Patent: Oct. 11, 2016

(54) LATEX PARTICLES FOR AGGLUTINATION ASSAY

(71) Applicant: SEKISUI MEDICAL CO., LTD., Tokyo (JP)

(72) Inventors: Shinichiro Kitahara, Tokyo (JP); Yuki Takahashi, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/389,182

(22) PCT Filed: Apr. 1, 2013

(86) PCT No.: PCT/JP2013/059987
§ 371 (c)(1),
(2) Date: Dec. 2, 2014

(87) PCT Pub. No.: WO2013/147306
PCT Pub. Date: Oct. 3, 2013

(65) Prior Publication Data
US 2015/0080542 A1    Mar. 19, 2015

(30) Foreign Application Priority Data
Mar. 30, 2012  (JP) .................. 2012-080188

(51) Int. Cl.
| | |
|---|---|
| *G01N 33/545* | (2006.01) |
| *C08L 33/14* | (2006.01) |
| *G01N 33/58* | (2006.01) |
| *C08F 212/08* | (2006.01) |
| *C08F 212/14* | (2006.01) |
| *C08F 220/28* | (2006.01) |

(52) U.S. Cl.
CPC .......... *G01N 33/585* (2013.01); *C08F 212/08* (2013.01); *C08F 212/14* (2013.01); *C08F 220/28* (2013.01)

(58) Field of Classification Search
CPC .. C08F 212/08; C08F 212/14; C08F 220/08; G01N 33/585
USPC .................................. 526/240, 286
See application file for complete search history.

(56) References Cited

U.S. PATENT DOCUMENTS

| | | | |
|---|---|---|---|
| 4,794,152 A | 12/1988 | Kobashi et al. | |
| 5,166,077 A | 11/1992 | Kihara et al. | |
| 5,714,340 A | 2/1998 | Sutton et al. | |
| 7,338,813 B2 | 3/2008 | Obana | |
| 7,867,785 B2 | 1/2011 | Obana | |
| 2004/0171176 A1* | 9/2004 | Obana ............ | C08F 212/08 436/533 |
| 2008/0113452 A1 | 5/2008 | Obana | |
| 2008/0181965 A1 | 7/2008 | Leon et al. | |

FOREIGN PATENT DOCUMENTS

| | | | | |
|---|---|---|---|---|
| EP | 0295402 A2 | 12/1988 | | |
| JP | 58-34486 | * 7/1983 | ............ | C08F 212/08 |
| JP | 58-34486 B2 | 7/1983 | | |
| JP | 3-44085 B2 | 7/1991 | | |
| JP | 6-26552 A | 9/1994 | | |
| JP | 6-82128 B2 | 10/1994 | | |
| JP | 8-10224 B2 | 1/1996 | | |
| JP | 2003-231648 A | 8/2003 | | |
| JP | 3706942 B2 | 10/2005 | | |
| WO | WO 2010/082681 A1 | 7/2010 | | |

OTHER PUBLICATIONS

International Preliminary Report on Patentability issued in International Application No. PCT/JP2013/059987 on Oct. 9, 2014.
International Search Report, mailed Jun. 4, 2013, issued in PCT/JP2013/059987.
Extended European Search Report, dated Sep. 30, 2015, for European Application No. 13769281.0.

\* cited by examiner

*Primary Examiner* — Ling Choi
*Assistant Examiner* — Chun-Cheng Wang
(74) *Attorney, Agent, or Firm* — Birch, Stewart, Kolasch & Birch, LLP

(57) ABSTRACT

A latex particle for high-sensitive agglutination assay and a reagent for agglutination assay including the particle are provided. The latex particle barely initiates non-specific reactions and can readily prepare diagnostic agents. A latex particle for agglutination assay including a polymerizable monomer having a phenyl group, a polymerizable monomer having a phenyl group and a salt of sulfonic acid, and a polymerizable monomer represented by Formula (1):

$$CH_2=CR_1-COO(CH_2CH_2O)_n-R_2 \qquad (1)$$

where $R_1$ represents a hydrogen atom or a methyl group; $R_2$ represents a hydrogen atom or a methyl group; and n is $1 \leq n < 20$, wherein the density of functional groups derived from the polymerizable monomer represented by Formula (1) on the surface of the particle is 0.05 to 0.5 μmol/m².

6 Claims, 1 Drawing Sheet

LATEX PARTICLES FOR AGGLUTINATION ASSAY

TECHNICAL FIELD

The present invention relates to latex particles for high-sensitive agglutination assay that barely initiate non-specific reactions, and a reagent for agglutination assay using the latex particles.

BACKGROUND ART

Immunoassays utilizing antigen-antibody reactions have been extensively performed to determine slight amounts of substances in samples in the field of clinical examination. Among these, latex immunoturbidimetry with latex particles carrying antibodies (hereinafter also referred to as sensitized latex particles) has been extensively used in laboratories because the latex immunoturbidimetry can be achieved by a simple operation for a short time. In latex immunoturbidimetry, the amount of an antigen or an antibody in a sample is determined through optical detection of a change in absorbance caused by agglutination of sensitized latex particles during formation of immune complexes. This change in absorbance is based on an apparent change in particle size caused by agglutination of the sensitized latex particles.

As described in Patent Document 1, polystyrene latex particles mainly composed of polystyrene have been used in latex immunoturbidimetry because of ease in immobilization (sensitization) of antigens or antibodies specifically reactive with their target substances, relatively low cost, and easy control of the polymerization reaction of these particles. Regardless of such an advantage, i.e., physical adsorption (sensitization) of antigens or antibodies, the polystyrene latex particles can also adsorb non-target proteins in samples. This adsorption of non-target proteins may cause so-called non-specific reactions, i.e., agglutination reactions of sensitized latex particles not caused by a specific antigen-antibody reaction. The non-specific reactions should be suppressed.

According to Patent Document 1, latex particles sensitized with an antigen or an antibody are blocked with bovine serum albumin (BSA) to suppress the non-specific reactions. Unfortunately, such blocking is still insufficient, and generates high background values. Accordingly, this measure has a severe challenge for preparation of reagents enabling highly sensitive measurement.

Patent Document 2 discloses preparation of carrier particles for diagnostic agents. The particles are prepared by copolymerization of styrene, a compound represented by the formula: $CH_2=CR_3-COO(CH_2CH_2O)_x(CH(CH_3)CH_2O)_y(CH_2CH_2O)_zR_4$, where $R_3$ represents H or $CH_3$; $R_4$ represents H or $CH_3$; x, y, and z each represent 0 or an integer of 100 or less, and satisfy a relation $1 \leq x+y+z \leq 100$, and a salt of styrenesulfonic acid in the presence of a water-soluble radical polymerization initiator in water. Patent Document 2 discloses use of only compounds represented by the formula where at least one of x, y, and z is 20 or more, and does not suggest use of any other compound. Furthermore, a high content of the compound represented by the formula is used in preparation of the polymer particles; hence, the resulting polymer particles barely adsorb antigens or antibodies physically onto their surfaces and cannot function as carrier particles for a diagnostic agent.

Patent Document 3 discloses latex particles suppressing non-specific adsorption prepared by co-immobilizing polyethylene glycols having different chain lengths and an antibody or an antigen onto the surfaces of the particles through covalent bonds to prevent desorption. Unfortunately, the latex particles should have a large number of functional groups for bonding antibodies and polyethylene glycol chains onto the surfaces of the particles, and should be prepared by a complicated process involving covalent bonding of antibodies, followed by covalent bonding of polyethylene glycol.

RELATED ART

Patent Document 1: Japanese Patent No. 3708942
Patent Document 2: Japanese Examined Patent Application Publication No. 58-34486
Patent Document 3: WO2010/082681

SUMMARY OF INVENTION

An object of the present invention, which has been made to solve the problems in traditional latex immunoturbidimetry, is to provide a latex particle for high-sensitive agglutination assay that barely initiates non-specific reactions and can readily prepare diagnostic agents and a reagent for agglutination assay including the latex particle.

Patent Document 2 specifies the monomers to be used only in terms of weight, and does not suggest or describe the optimal amount (density) of the ethylene glycol (containing) monomer and the optimal amount (density) of the propylene glycol (containing) monomer bonded onto the surfaces of latex particles. For this reason, optimal amounts of the monomers should be determined by trial and error depending on the molecular weights of the monomers in examination on synthetic conditions that can sufficiently suppress the non-specific reactions. Patent Document 3 requires a step of bonding an ethylene glycol (containing) monomer in addition to a step of preparing latex particles, resulting in a complicated two-stage operation involving control of functional groups for bonding ethylene glycol during the preparation of the latex particles and control of bonding of the functional groups to ethylene glycol.

Solution to Problem

The present inventors, who have conducted extensive research to solve the problems, have prepared a latex particle for agglutination assay according to the present invention through a simple operation simultaneously with synthesis of a latex particle. The present invention is characterized as follows.

Aspect [1]. A latex particle for agglutination assay, including a polymerizable monomer having a phenyl group, a polymerizable monomer having a phenyl group and a salt of sulfonic acid, and a polymerizable monomer represented by Formula (1), wherein the density of functional groups in the polymerizable monomer represented by Formula (1) on the surface of the particle is 0.05 to 0.5 µmol/m²:

$$CH_2=CR_1-COO(CH_2CH_2O)_n-R_2 \qquad (1)$$

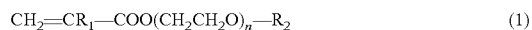

where $R_1$ represents a hydrogen atom or a methyl group; $R_2$ represents a hydrogen atom or a methyl group; and n is $1 \leq n < 20$.

Aspect [2]. The latex particle for agglutination assay according to Aspect [1], wherein the polymerizable monomer having the phenyl group is at least one selected from the group consisting of styrene, o-methylstyrene, p-methylstyrene, p-chlorostyrene, and 4-vinylbenzoic acid.

Aspect [3]. The latex particle for agglutination assay according to Aspect [1] or [2], wherein the polymerizable monomer having the phenyl group and the salt of sulfonic acid is at least one selected from the group consisting of salts of styrenesulfonic acid, salts of divinylbenzenesulfonic acid, salts of o-methylstyrenesulfonic acid, and salts of p-methylstyrenesulfonic acid.

Aspect [4]. The latex particle for agglutination assay according to Aspect [1], wherein the polymerizable monomer having the phenyl group is styrene, and the polymerizable monomer having the phenyl group and the salt of sulfonic acid is sodium styrenesulfonate.

Aspect [5]. The latex particle for agglutination assay according to Aspect [1], wherein the latex particle carries an antigen or an antibody through physical adsorption.

Aspect [6]. A reagent for agglutination assay including the latex particle for agglutination assay according to any one of Aspects [1] to [5].

Effects of Invention

The latex particle for agglutination assay and the reagent for agglutination assay according to the present invention cause only a target specific agglutination reaction without adsorption of non-target proteins causing non-specific agglutination reactions and thus can produce a diagnostic agent more sensitive than traditional ones. The latex particle can be prepared by a single-stage polymerization reaction, and is designed to be sensitized with an antigen or an antibody through physical adsorption thereof. For this reason, a highly sensitive particle can be prepared by a significantly simple process also in preparation of diagnostic agents.

DESCRIPTION OF EMBODIMENT

Figure 1:
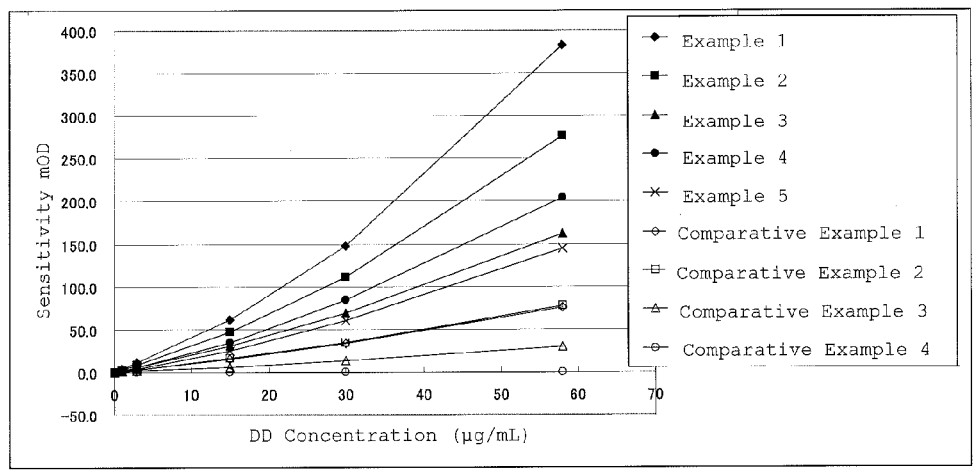
FIG. 1 is calibration curves produced by measurement of standard D-dimer antigens with latex particles for agglutination assay sensitized with anti-D-dimer antibodies in Examples and Comparative Examples.

The present inventors, who have conducted extensive research to solve the problems, provide a latex particle for agglutination assay including a polymerizable monomer having a phenyl group, a polymerizable monomer having a phenyl group and a salt of sulfonic acid, and polyethylene glycol(meth)acrylate (hereinafter referred to as "PEG monomer") having a terminal hydroxyl group or methyl group, wherein the density of functional groups in the PEG monomer on the surface of the particle is 0.05 to 0.5 μmol/m².

The present invention now will be described in more detail. The latex particle for agglutination assay according to the present invention contains any polymerizable monomer having a phenyl group. Examples thereof include styrene, o-methyl styrene, p-methylstyrene, p-chlorostyrene, and 4-vinylbenzoic acid. These may be used alone or in combination. Among these, preferred is styrene.

The polymerizable monomer having a phenyl group and a salt of sulfonic acid can be any monomer which enables a sulfonate group to be present on the surface of the particle after polymerization. Examples of such monomers include salts of styrenesulfonic acid, salts of divinylbenzenesulfonic acid, salts of o-methylstyrenesulfonic acid, and salts of p-methylstyrenesulfonic acid. Here, any sulfonic acid salt can be used. Examples thereof include sodium salts, potassium salts, lithium salts, and ammonium salts. These salts may be used alone or in combination. Among these, preferred are salts of styrenesulfonic acid, and more preferred is sodium styrenesulfonate.

The PEG monomer can be any monomer represented by Formula (1):

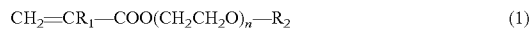

$$CH_2=CR_1-COO(CH_2CH_2O)_n-R_2 \quad (1)$$

where $R_1$ represents a hydrogen atom or a methyl group; $R_2$ represents a hydrogen atom or a methyl group; and n is $1 \leq n < 20$.

Examples thereof include Blemmer (Registered Trademark, the same holds true below) PE-90 ($R_1$=methyl group, $R_2$=H, n=2, available from NOF CORPORATION), Blemmer PE-200 ($R_1$=methyl group, $R_2$=H, n=4 to 5, available from NOF CORPORATION), Blemmer PE-350 ($R_1$=methyl group, $R_2$=H, n=8, available from NOF CORPORATION), Blemmer AE-90 ($R_1$=H, $R_2$=H, n=2, available from NOF CORPORATION), Blemmer AE-200 ($R_1$=H, $R_2$=H, n=4 to 5, available from NOF CORPORATION), Blemmer AE-400 ($R_1$=H, $R_2$=H, n=10, available from NOF CORPORATION), Blemmer PME-100 ($R_1$=methyl group, $R_2$=methyl group, n=2, available from NOF CORPORATION), Blemmer PME-200 ($R_1$=methyl group, $R_2$=methyl group, n=4, available from NOF CORPORATION), Blemmer PME-400 ($R_1$=methyl group, $R_2$=methyl group, n=9, available from NOF CORPORATION), Blemmer AME-400 ($R_1$=H, $R_2$=methyl group, n=9, available from NOF CORPORATION), LIGHT ACRYLATE MTG-A ($R_1$=H, $R_2$=methyl group, n=3, available from Kyoeisha Chemical Co., Ltd.), LIGHT ACRYLATE 130A ($R_1$=H, $R_2$=methyl group, n=9, available from Kyoeisha Chemical Co., Ltd.).

The latex particles according to the present invention are prepared by soap-free emulsion polymerization in an aqueous medium containing the polymerizable monomer having a phenyl group, the polymerizable monomer having a phenyl group and a salt of sulfonic acid, and the PEG monomer. Such polymerization can be conducted by any known soap-free emulsion polymerization process. For example, the polymerizable monomer having the phenyl group, the polymerizable monomer having a phenyl group and a salt of sulfonic acid, the PEG monomer, and a polymerization initiator are added to water as a medium in a reaction container, and the reaction mixture is heated with stirring under a nitrogen atmosphere.

The polymerization temperature is preferably 50 to 100° C., more preferably 60 to 85° C. The polymerization time depends on conditions, such as the composition of the polymerizable monomers and the contents thereof, and the polymerization initiator, and is usually 5 to 50 hours.

A preferred aqueous medium is water (deionized water) alone or a mixed solvent of water and a water-miscible solvent. Examples of the mixed solvent include mixed solvents of water and alcohols, such as ethanol. Among these, preferred is water alone.

A known radical initiator can be used as the polymerization initiator. Examples thereof include persulfates, such as potassium persulfate, sodium persulfate, and ammonium persulfate; azo compounds, such as 2,2'-azobisisobutyronitrile, 2,2'-azobis(4-methoxy-2,4-dimethylvaleronitrile), and 2,2'-azobis-2,4-dimethylvaleronitrile; and organic peroxides, such as benzoyl peroxide, di-t-butyl peroxide, lauroyl peroxide, and t-butylperoxy-2-ethylhexanoate. Among these, preferred are persulfates, more preferred is potassium persulfate. The polymerization initiator can be used in any content. A preferred content of the polymerization initiator is in the range of 0.01 to 5 wt % relative to the polymerizable monomers.

Depending on applications of the latex particle for agglutination assay according to the present invention, a polymerizable unsaturated monomer copolymerizable with the monomers described above may further be added during polymerization. Such a polymerizable unsaturated monomer can be any monomer typically used in radical polymerization. Examples thereof include (meth)acrylic acid, (meth)acrylate esters, styrene derivatives, (meth)acrylonitrile, (meth)acrylic acid amides, halogenated vinyls, vinyl esters, (meth)acrolein, maleic acid derivatives, and fumaric acid derivatives. Throughout the specification, the term (meth)acrylic acid indicates acrylic acid or methacrylic acid. The styrene derivatives indicate styrene derivatives other than the polymerizable monomer having the phenyl group and the polymerizable monomer having the phenyl group and the salt of sulfonic acid used in the present invention.

In the present invention, the PEG monomer can be used in polymerization in any amount such that the density of the functional groups in the PEG monomer on the surfaces of the particles is 0.05 to 0.5 μmol/m². A higher density of the functional groups on the surfaces of the particles is not preferred regardless of its high effect of suppressing non-specific reactions because such a higher density reduces sensitivity significantly. A significantly low density of the functional groups on the surfaces of the particles is not preferred because such a low density reduces the effect of suppressing non-specific reactions by the PEG monomer and the resulting latex particles are not superior to latex particles not containing the PEG monomer in the effect of suppressing non-specific reactions. The present inventors have found that it is important to control the density of the functional groups of the PEG monomer to be 0.05 to 0.5 μmol/m² to suppress non-specific reactions without a reduction in sensitivity, and have completed the present invention.

The density of the functional group of the PEG monomer is calculated from the following expression:

Density of the functional groups (μmol/m²)=(molar amount of PEG monomer used in preparation of latex particles)/(total surface area of prepared latex particles)

The density of the functional group can be calculated by the following procedure:
Let r represent the average particle size (nm) of the prepared latex particles,
Y represent the molar amount (μmol) of the PEG monomer used in preparation of the latex particles, or
Y=(weight (g) of the PEG monomer used in preparation)/(average molecular weight of the PEG monomer used in preparation),
V represent the total volume (cm³) of the latex particles,
S represent the total surface area (cm²) of the latex particles,
x represent the total number of the latex particles,
Z represent the density of the functional groups (μmol/m²), and
K represent the total weight (g) of the polymerizable monomer having the phenyl group, the polymerizable monomer having the phenyl group and the salt of sulfonic acid, the polymerization initiator, and the PEG monomer used in the polymerization reaction, V and S are calculated as follows:

$$V = 4/3\pi(r/2\times 10^{-7})^3 \times x,$$

and $$S = 4\pi(r/2\times 10^{-7})^2 \times x$$

lead to $S = 6V/(r\times 10^{-7})$;

then, $$Z = Y/(S\times 10^{-4}) = Y\times r\times 10^{-3}/6V;$$

where the specific gravity of polystyrene polymerized is 1.06 g/cm³,
V=K/1.06, and
Z=1.766×10⁻⁴×Y×r/K.

The average particle size of the latex particles according to the present invention for agglutination assay is desirably 0.05 to 1.0 μm. An average particle size of less than 0.05 μm cannot attain sensitivity needed for measurement due to a significantly small amount of optical change caused by agglutination of the latex particles, and increases the time for centrifugation during preparation of the reagent to increase cost of the reagent. With an average particle size of the latex particles more than 1.0 μm and a high concentration of a target substance, the optical change caused by agglutination of the latex particles exceeds the measurable range, and the measured amount of the optical change does not correspond to the amount of the target substance. The average particle size depends on the method and the apparatus used in the measurement using the latex particles for agglutination assay. The average particle size is preferably 0.05 to 0.7 μm, more preferably 0.05 to 0.4 μm.

The coefficient of variation (CV value) in diameter of the latex particles is preferably 20% or less. A coefficient of variation of more than 20% may cause low reproductivity between production lots during preparation of reagents, and thus reduce the reproductivity of the reagent for assay. The coefficient of variation is more preferably 15% or less. The coefficient of variation in particle diameter is determined from the following equation:

Coefficient of variation in particle diameter (CV value)=(standard deviation of the particle diameters)/(average particle size)

The density of the functional groups, which represents the density of the PEG monomer on the surfaces of the latex particles for agglutination assay according to the present invention, can be controlled by the molar amount of the PEG monomer used in preparation of the latex particles. Namely, the amount of the functional groups on the surfaces of the latex particles per unit area is specified in terms of the molar amount rather than the weight of the PEG monomer used in preparation of the latex particles. The density of the functional groups can be determined by a simple operation from any PEG monomer having a different molecular weight as long as it can be represented by Formula (1):

$$CH_2=CR_1-COO(CH_2CH_2O)_n-R_2 \qquad (1)$$

where $R_1$ represents a hydrogen atom or a methyl group; $R_2$ represents a hydrogen atom or a methyl group; and n is $1\leq n<20$ The latex particles for agglutination assay according to the present invention are obtained in a state in which the latex particles are suspended in water or an aqueous solvent. The particles can be used in any content. The content is usually 1 to 20 wt %. At a content of less than 1 wt %, the reagent should be concentrated during preparation thereof. At a content of more than 20 wt %, the particles agglutinate.

Another aspect of the present invention is a latex particle for agglutination assay that carries a substance specifically bonding to a target substance through physical adsorption. The substance specifically bonding to a target substance can be any reagent for immunoserological tests (reagents used in immunological agglutination reactions and agglutination-inhibiting reactions) or any physiologically active substance typically used in biochemical assays. Among these, substances used in antigen-antibody reactions are suitable.

Examples of the substances used in antigen-antibody reactions include antigens or antibodies, such as proteins, nucleic acids, nucleoproteins, estrogen, and lipids. Examples of antigens include a variety of antigens, receptors, and enzymes, such as β2-microglobulin, C-reactive protein (CRP), insulin, human fibrinogen, ferritin, rheumatoid factor (RA), α-fetoprotein (AFP), mycoplasma antigen, and HBs antigen. Examples of antibodies include a variety of antibodies against toxins and disease germs, such as anti-streptolisyn O antibody, anti-estrogen antibody, anti-β2-microglobulin antibody, anti-*Treponema pallidum* antibody, antibody against syphilis lipid antigen, anti-HBs antibody, anti-HBc antibody, anti-HBe antibody, anti-PSA antibody, anti-CRP antibody, anti-insulin antibody, and anti-D-dimer antibody. The antibodies can be immunoglobulin molecules themselves or fragments thereof, such as $F(ab')_2$. The antibodies to be used can be polyclonal antibodies or monoclonal antibodies.

A substance specifically reactive with a target substance can be carried on (sensitized to) the latex particles by any known process as long as the immobilization, or the sensitization, is carried out through physical adsorption.

The substance carried on the latex particles can be optionally blocked with bovine serum albumin and be dispersed in an appropriate buffer to prepare a dispersion of sensitized latex particles. The dispersion of sensitized latex particles, a buffer, and a standard substance to be used in measurement can be used as a kit of reagents for agglutination assay.

The substance specifically reactive with a target substance can be carried on the latex particles in any amount. The amount depends on the type of the substance specifically reactive with a target substance.

For use of a reagent for assay including the latex particles carrying an antigen or an antibody, the reagent can contain a variety of sensitizers to enhance the sensitivity for assay and promote an antigen-antibody reaction. Examples of the sensitizers include alkylated polysaccharides, such as methyl cellulose and ethyl cellulose; pullulan; and polyvinylpyrrolidone.

The latex particles according to the present invention can highly suppress the non-specific reactions. Furthermore, the latex particles may contain proteins, such as albumin (bovine serum albumin, ovalbumin), casein, and gelatin, and decomposed products thereof, amino acid, or a surfactant to suppress the non-specific reactions caused by other substances existing in samples or to enhance the stability of the reagent.

The target substance may be diluted with an appropriate diluent. The diluent can be any buffer at a pH of 5.0 to 9.0. Examples thereof include phosphate buffers, glycine buffers, tris buffers, borate buffers, and citrate buffers.

The reagent for assay including the latex particle according to the present invention carrying an antigen or an antibody can determine the reaction amount of the target substance in a sample by optically measuring the degree of agglutination of the latex particle caused by specific reaction of the target substance in the sample with the substance reactive with the target substance carried on the latex particles. The optical measurement can be conducted with any of standard biochemical automatic analyzers, such as optical detectors that can detect the intensity of scattered light, the intensity of transmitted light, and the absorbance, or any optical apparatus provided with these detectors in combination.

The degree of agglutination can be optically determined by any known method. Examples thereof include turbidimetry that detects agglutination as an increase in turbidity, a method that detects agglutination as a change in particle size distribution or average particle size, and a method that detects integrating sphere turbidity in which a change in forward-scattered light caused by agglutination is measured with an integrating sphere, and then compared with the intensity of transmitted light.

Examples of the method of measuring the change in the degree of agglutination also include rate assays in which at least two values are obtained from measurement at different times, and the degree of agglutination is determined based on an increase between these two values measured at different times (a rate of increase); and end point assays in which one value is obtained from measurement at one time (typically a time considered as the end point of the reaction), and the degree of agglutination is determined from the obtained value. Among these, end point assays according to turbidimetry are suitable because the operation is simple and speedy.

EXAMPLES

The present invention will now be described in more detail by way of Examples. The particle sizes of the latex for agglutination assay prepared in Examples were each measured as follows.

Measurement of Particle Size of Latex for Agglutination Assay:

The latex particles for agglutination assay were put onto a collodion film by a normal method. Images of particles were photographed with a transmission electron microscope, and the particle diameters (of 100 particles or more) on the images were measured to determine the average particle size and the standard deviation.

Example 1

Ultrapure water (1000 g), a styrene monomer (135 g), Blemmer PE-90 ($R_1$=methyl group, $R_2$=H, n=2, available from NOF CORPORATION) (0.24 g), sodium styrenesulfonate (1.2 g), and potassium persulfate (0.7 g) were placed in a glass reactor (volume: 2 L) provided with a stirrer, a refluxing cooler, a temperature detector, a nitrogen inlet pipe, and a jacket. After the container was purged with nitrogen gas, the mixed solution was polymerized for 24 hours at 70° C. with stirring at 210 rpm.

After the polymerization was terminated, the solution was filtered through a filter paper to extract latex particles. The latex particles were dialyzed through a dialyzing membrane for 48 hours to refine the latex particles. The latex particles had a particle size of 0.109 μm (CV: 8.4%) and a PEG density of 0.192 μmol/m².

Example 2

Latex particles were prepared as in Example 1 except that Blemmer PE-90 ($R_1$=methyl group, $R_2$=H, n=2, from NOF CORPORATION) (0.24 g) was replaced with Blemmer PE-200 ($R_1$=methyl group, $R_2$=H, n=4 to 5, available from NOF CORPORATION) (0.39 g). The latex particles had a particle size of 0.108 μm (CV: 11.7%) and a PEG density of 0.191 μmol/m².

Example 3

Latex particles were prepared as in Example 1 except that Blemmer PE-90 ($R_1$=methyl group, $R_2$=H, n=2, available from NOF CORPORATION) (0.24 g) was replaced with Blemmer PE-350 ($R_1$=methyl group, $R_2$=H, n=8, available from NOF CORPORATION) (0.60 g). The latex particles had a particle size of 0.106 μm (CV: 9.8%) and a PEG density of 0.187 μmol/m².

Example 4

Latex particles were prepared as in Example 1 except that Blemmer PE-90 ($R_1$=methyl group, $R_2$=H, n=2, available from NOF CORPORATION) (0.24 g) was replaced with Blemmer PE-200 ($R_1$=methyl group, $R_2$=H, n=4 to 5, available from NOF CORPORATION) (0.12 g). The latex particles had a particle size of 0.101 μm (CV: 10.5%) and a PEG density of 0.054 μmol/m².

Example 5

Latex particles were prepared as in Example 1 except that Blemmer PE-90 ($R_1$=methyl group, $R_2$=H, n=2, available from NOF CORPORATION) (0.24 g) was replaced with Blemmer PE-200 ($R_1$=methyl group, $R_2$=H, n=4 to 5, available from NOF CORPORATION) (0.98 g). The latex particles had a particle size of 0.105 μm (CV: 10.1%) and a PEG density of 0.464 μmol/m².

Comparative Example 1

Latex particles were prepared as in Example 1 except that Blemmer PE-90 ($R_1$=methyl group, $R_2$=H, n=2, available from NOF CORPORATION) (0.24 g) was not used. The latex particles had a particle size of 0.107 μm (CV: 10.3%). Since the PEG monomer was not used, the PEG density was 0.

Comparative Example 2

Latex particles were prepared as in Example 1 except that Blemmer PE-90 ($R_1$=methyl group, $R_2$=H, n=2, available from NOF CORPORATION) (0.24 g) was replaced with Blemmer PE-200 ($R_1$=methyl group, $R_2$=H, n=4 to 5, available from NOF CORPORATION) (0.03 g). The latex particles had a particle size of 0.104 μm (CV: 9.5%) and a PEG density of 0.018 μmol/m².

Comparative Example 3

Latex particles were prepared as in Example 1 except that Blemmer PE-90 ($R_1$=methyl group, $R_2$=H, n=2, available from NOF CORPORATION) (0.24 g) was replaced with Blemmer PE-200 ($R_1$=methyl group, $R_2$=H, n=4 to 5, available from NOF CORPORATION) (1.59 g). The latex particles had a particle size of 0.106 μm (CV: 11.3%) and a PEG density of 0.749 μmol/m².

Comparative Example 4

Latex particles were prepared as in Example 1 except that Blemmer PE-90 ($R_1$=methyl group, $R_2$=H, n=2, available from NOF CORPORATION) (0.24 g) was replaced with Blemmer PE-200 ($R_1$=methyl group, $R_2$=H, n=4 to 5, available from NOF CORPORATION) (4.05 g). The latex particles had a particle size of 0.106 μm (CV: 9.3%) and a PEG density of 1.891 μmol/m².

[Application]

A D-dimer reagent was evaluated with the latex particles prepared in Examples and Comparative Examples. The following reagent and materials were used.

<Reagent and Materials>
Anti-D-dimer antibody
Buffer for preparing a latex particle carrying an antibody: 20 mM Tris-HCl (pH: 8.0) was used.
Buffer for blocking: 2% BSA in 20 mM Tris-HCl (pH: 8.0) was used.
Buffer for diluting a sample: 0.15% BSA in 30 mM Tris-HCl (pH: 8.5) was used.

<Preparation of Reagent for Measuring D-Dimer>

After the latex particles prepared in Examples 1 to 5 and Comparative Examples 1 to 4 were each refined by centrifugation, the latex particles were each diluted to 5% (w/v) with Buffer for preparing a latex particle carrying an antibody to prepare a diluted latex solution.

Anti-D-dimer antibody was diluted to 1 mg/mL with Buffer for preparing a latex particle carrying an antibody to prepare a diluted antibody solution.

The diluted antibody solution (1 volume) was added to the diluted latex solution (1 volume) while the diluted latex solution was being stirred. The mixed solution was further stirred. Buffer for blocking (2 volumes) was further added, and the mixed solution was continuously stirred. The solution was recovered, and was adjusted to 0.50 (w/v) with a buffer to prepare a dispersion of antibody-sensitized latex particles. A D-dimer antigen standard solution was measured with the dispersion of antibody-sensitized latex particles to produce a calibration curve.

Apparatus: Hitachi 7170 automatic analyzer
Wavelength: 570/800 nm
Operating temperature: 37° C.
Target substance (0 to 58 μg/mL D-dimer standard solution): 12 μL
First reagent (Tris buffer containing 0.15 wt % bovine serum albumin): 100 μL
Second reagent (dispersion of 0.5% antibody-sensitized latex particles): 100 μL
Points for measurement: 18-34

[Measurement 1]

Measurement was performed with the antibody-sensitized latex particles (0.5% (w/v)) sensitized with Anti-D-dimer antibody in Examples 1 to 5 and Comparative Examples 1 to 4 according to the method described above to produce calibration curves (FIG. 1). FIG. 1 evidently shows that the antibody-sensitized latex particles in Examples 1 to 5 enable relatively high-sensitive assay. FIG. 1 also shows that the antibody-sensitized latex particles in Comparative Examples 1 to 4 have sensitivity lower than that of the antibody-sensitized latex particle in Example 2.

[Measurement 2]

Figure 2:
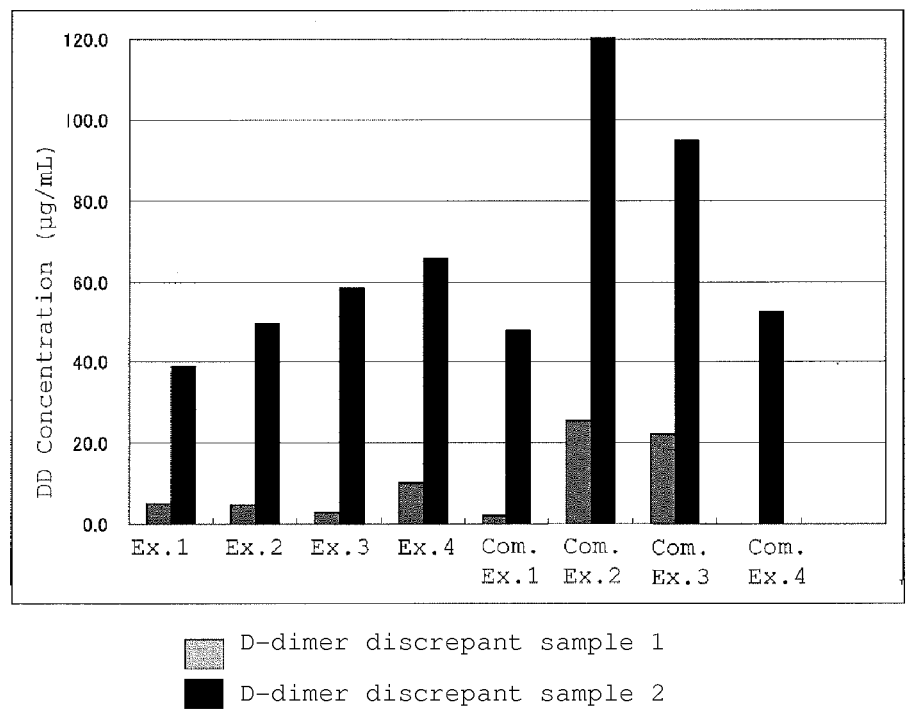
FIG. 2 is a graph showing the concentrations of D-dimers in D-dimer discrepant Samples 1 and 2 determined with the latex particles for agglutination assay sensitized with anti-D-dimer antibodies according to Examples and Comparative Examples, the concentrations being converted with the calibration curves in FIG. 1.

Diagnostic agent particles (0.5% (w/v)) in Examples 1 to 5 and Comparative Examples 1 to 4 sensitized with Anti-D-dimer antibody and two D-dimer discrepant samples were subjected to the measurement according to the method described above, and the observed values were converted into the concentrations of the D-dimers with the calibration curves produced in Measurement 1. Here, a D-dimer discrepant sample is a sample in which a non-specific agglutination reaction was observed in a system measured by the traditional immunoturbidimetry of the D-dimer. The results are shown in FIG. 2. FIG. 2 evidently shows that the antibody-sensitized latex particles in Examples 1 to 5 more significantly suppress the non-specific agglutination reactions in D-dimer discrepant Samples than the latex particle in Comparative Example 1 not containing the PEG monomer does. FIG. 2 also shows that the antibody-sensitized latex particles in Comparative Examples 2 to 4 equally or more significantly suppress the non-specific agglutination reactions in D-dimer discrepant samples than the antibody-sensitized latex particles in Examples 1 to 5 do, whereas the sensitivity is significantly reduced as shown in Measurement 1 and particularly, negative values were obtained in the measurement in Comparative Examples 3 and 4. The reason for insufficient sensitivity in Comparative Examples is probably because the surfaces of the latex particles do not adsorb (are not sensitized with) the antibody sufficiently.

INDUSTRIAL APPLICABILITY

The latex particle for agglutination assay together with the reagent for agglutination assay, according to the present invention, can cause only the target specific agglutination reaction without adsorbing non-target proteins in samples which cause the non-specific agglutination reactions. Accordingly, the latex particle for agglutination assay and the reagent for agglutination assay according to the present invention can provide a diagnostic agent more sensitive than traditional ones. The latex particle for agglutination assay and the reagent for agglutination assay according to the present invention are useful as reagents for immunoserological tests (reagents used in immunological agglutination reactions and agglutination-inhibiting reactions) and reagents for testing physiologically active substances typically used in biochemical assays.

The invention claimed is:
1. A latex particle for agglutination assay, comprising:
a polymerizable monomer having a phenyl group,
a polymerizable monomer having a phenyl group and a salt of sulfonic acid, and
a polymerizable monomer represented by Formula (1):

$$CH_2=CR_1-COO(CH_2CH_2O)_n-R_2 \quad (1)$$

where $R_1$ represents a hydrogen atom or a methyl group; $R_2$ represents a hydrogen atom or a methyl group; and n is $1 \leq n < 20$,
wherein the density of functional groups derived from the polymerizable monomer represented by Formula (1) on the surface of the particle is 0.05 to 0.5 $\mu mol/m^2$.

2. The latex particle for agglutination assay according to claim 1, wherein the polymerizable monomer having the phenyl group is at least one selected from the group consisting of styrene, o-methylstyrene, p-methylstyrene, p-chlorostyrene, and 4-vinylbenzoic acid.

3. The latex particle for agglutination assay according to claim 1 or 2, wherein the polymerizable monomer having the phenyl group and the salt of sulfonic acid is at least one selected from the group consisting of salts of styrenesulfonic acid, salts of divinylbenzene sulfonic acid, salts of o-methylstyrenesulfonic acid, and salts of p-methylstyrenesulfonic acid.

4. The latex particle for agglutination assay according to claim 1, wherein the polymerizable monomer having the phenyl group is styrene, and the polymerizable monomer having the phenyl group and the salt of sulfonic acid is sodium styrenesulfonate.

5. The latex particle for agglutination assay according to claim 1, wherein the latex particle carries an antigen or an antibody through physical adsorption.

6. A reagent for agglutination assay comprising the latex particle for agglutination assay according to claim 1.

* * * * *